US010169542B2

(12) United States Patent
Choi et al.

(10) Patent No.: US 10,169,542 B2
(45) Date of Patent: Jan. 1, 2019

(54) SYSTEMS AND METHODS FOR AUTOMATICALLY DETERMINING MYOCARDIAL BRIDGING AND PATIENT IMPACT (71) Applicant: HeartFlow, Inc., Redwood City, CA (US)

(72) Inventors: Gilwoo Choi, Mountain View, CA (US); Charles A. Taylor, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/181,894

(22) Filed: Jun. 14, 2016

(65) Prior Publication Data

US 2016/0292383 A1    Oct. 6, 2016

Related U.S. Application Data (63) Continuation of application No. 14/535,755, filed on Nov. 7, 2014, now Pat. No. 9,390,224.

(60) Provisional application No. 62/043,841, filed on Aug. 29, 2014.

(51) Int. Cl.
G06F 19/00     (2018.01)
A61B 6/00      (2006.01)
G16H 50/50     (2018.01)
G06F 19/12     (2011.01)
A61B 5/02      (2006.01)
A61B 5/026     (2006.01)
A61B 5/00      (2006.01)

(52) U.S. Cl.
CPC ........ G06F 19/3437 (2013.01); A61B 5/0044 (2013.01); A61B 5/02028 (2013.01); A61B 6/503 (2013.01); A61B 6/504 (2013.01); A61B 6/507 (2013.01); A61B 6/5217 (2013.01); G06F 19/00 (2013.01); G06F 19/12 (2013.01); G16H 50/50 (2018.01); A61B 5/02007 (2013.01); A61B 5/0263 (2013.01); A61B 5/4836 (2013.01); A61B 5/4848 (2013.01)

(58) Field of Classification Search
None
See application file for complete search history.

(56) References Cited

U.S. PATENT DOCUMENTS

| 8,249,815 | B2 | 8/2012 | Taylor |
| 2007/0274579 | A1 | 11/2007 | Cai et al. |
| 2012/0041318 | A1 | 2/2012 | Taylor |
| 2013/0197881 | A1 | 8/2013 | Mansi et al. |
| 2015/0112182 | A1 | 4/2015 | Sharma et al. |

FOREIGN PATENT DOCUMENTS

EP    2 690 598 A2    1/2014

OTHER PUBLICATIONS

Jeong Y. H. et al.: "A head-to-head comparison between 64-slice multidetector computed tomographic and conventional coronary angiographies in measurement of myocardial bridge", vol. 143, No. 3, Sep. 3, 2010, pp. 243-248.
International Search Report and Written Opinion for corresponding PCT Application No. PCT/US2015/045910, dated Oct. 28, 2015, (14 pages).
Hwang et al. (Korean J. Radial. (201 0) vol. 11 (5):514-521 ).
Mohlenkamp et al. (Circulation (2002) vol. 1 06:2616-2622).
Ge and Ma ((2011) Detection Myocardial Bridging Using Non-Invasive technique, Coronary Angiography-Advances in Noninvasive Imaging Approach for Evaluation of Cornoary Artery Disease, Prof. Baskot Branislav (Ed.), ISBN 978-953-307-675-1, in Tech. (V) con't.= Available from http://www.intechopen.com/books/coronary-angiography-advances-in-noninvasive-imaging-approach forevaluation-of-coronary-artery-disease/detection-myocardial-bridging-using-non-invasive-technique; Chapter 10, pp. 183-198).
Alegria et al. European Heart Journal (2005) vol. 26:1159-1168 teaching a review of myocardial bridging, imaging techniques for myocardial bridging and treatments.
Dong et al. 35th Annual International Conference of the IEEE EMBS, Osaka, Japan, Jul. 3-7, 2013:1402-1405.
Escaned et al. Journal of the American College of Cardiology (2003) vol. 42:226-233.
Ge et al. British Heart Journal (1995) vol. 73:462-465.
Ge et al. European Heart Journal (1999) vol. 20:1707-1716.
Itu et al. 9th International Symposium on Biomedical Imaging (ISBI) (2012), IEEE, May 2, 2012: 832-835.
Montillo Shape Prior in Medical Image Analysis: Extensions of the Level Set Method (2000) in Univ. of Penn Scholarly Commons, Technical Report (MS-CIS-02-08), Department of Computer & Information Science, Nov. 2000:1-56.
Niu et al. Experimental and Therapeutic Medicine (2013) vol. 5:848-852; published online on Dec. 28, 2012.
Park et al. Canadian Journal of Cardiology (2011) vol. 27:596-600.
Parodi et al. Ieee Transactions on Information Technology in Biomedicine Sep. 2012, vol. 16:952-965.
Jeong Y H et al.: "A head-to-head comparison between 64-slice multidetector computed tomographic and conventional coronary angiographies in measurement of myocardial bridge", International Journal of Cardiology, Elsevier Science Publishers, Amsterdam, NL, vol. 143, No. 3, Sep. 3, 2010, pp. 243-248.
So Yeon Kim et al.: "Evaluation of Myocardial Bridge with Multidetector Computed Tomography", vol. 74, No. 1, Dec. 5, 2009, pp. 137-141.

Primary Examiner — Lori A. Clow
(74) Attorney, Agent, or Firm — Bookoff McAndrews, PLLC (57)    ABSTRACT Embodiments include computer-implemented methods and systems for reporting the presence of myocardial bridging in a patient, the method comprising detecting, within a patient-specific model representing at least a portion of the patient's heart based on patient-specific anatomical image data regarding a geometry of the patient's heart, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

20 Claims, 11 Drawing Sheets

FIG. 9

SYSTEMS AND METHODS FOR AUTOMATICALLY DETERMINING MYOCARDIAL BRIDGING AND PATIENT IMPACT

PRIORITY

This application is a continuation of U.S. application Ser. No. 14/535,755, filed Nov. 7, 2014, which claims the benefit of priority to U.S. Provisional Application No. 62/043,841 filed Aug. 29, 2014, all of which are incorporated herein by reference in their entireties.

TECHNICAL FIELD

Embodiments of the present disclosure include methods and systems for modeling of fluid flow and, more particularly, methods and systems for patient-specific modeling and evaluation of blood flow.

BACKGROUND

Myocardial bridging is a congenital coronary abnormality in which a coronary segment runs through the myocardium intramurally (e.g., a segment of a coronary artery tunnels through the myocardium instead of lying on top of it), resulting in systolic compression of the tunneled segment. The frequency of myocardial bridging has been reported to be 1.5% to 16% in coronary angiography and as high as 80% in autopsy series. Myocardial bridging can cause cardiac-related complications such as ischemia and acute coronary syndromes, and coronary spasms.

Coronary artery disease, in turn, may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

Myocardial bridging may occur partially or completely. For example, a segment of a coronary artery of a patient may be completely surrounded by the patient's myocardium (e.g., 100% tunneling of the vessel into the myocardium). Alternatively, the abnormality may occur as partial myocardial bridging—e.g., 30%-99% of the circumference of a segment of a coronary artery of the patient is surrounded by the myocardium, with tapering and/or reduction of cross-sectional area of the coronary artery.

Typically, myocardial bridging may be diagnosed by coronary angiography or intravascular ultrasound imaging (IVUS) based on one or more of several features, including significant percent lumen diameter narrowing, persistent diastolic diameter reduction, a "milking effect" in angiography, and/or a "half moon" phenomenon in IVUS. Besides morphological evaluation, intracoronary Doppler may show increased flow velocity, retrograde systolic flow, and reduced coronary flow reserve in myocardial bridging. The functional significance of myocardial bridging may be evaluated using fractional flow reserve (FFR) with the use of inotropic agents. FFR may be defined as the ratio of the mean blood pressure and/or flow downstream of a location, such as a lesion or location of myocardial bridging, divided by the mean blood pressure and/or flow upstream from the location, under conditions of increased coronary blood flow, e.g., when induced by intravenous administration of adenosine.

However, traditionally, these methods are invasive procedures and may involve the use of inotropic agents such as dobutamine to induce maximal myocardial contraction. In some cases, diastolic FFR may be more relevant than the conventional FFR to the evaluation of myocardial bridging due to overshooting of systolic pressure, which may lead to underestimation of severity when assessed by the conventional FFR.

As these physiologic and hemodynamic conditions of myocardial bridging may hamper the use of conventional invasive FFR, it would be useful to differentiate patients with fixed stenosis from those with myocardial bridging for an accurate blood flow simulation in assessing the hemodynamic significance of lesions.

It is to be understood that both the foregoing general description and the following detailed description are exemplary and explanatory only and are not restrictive of the disclosure.

SUMMARY

In accordance with an embodiment, a computer-implemented method for reporting the presence of myocardial bridging in a patient includes receiving patient-specific anatomical image data regarding a geometry of the patient's heart; creating a patient-specific model representing at least a portion of the patient's heart based on the patient-specific anatomical image data; detecting, within the patient-specific model, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

In accordance with another embodiment, a system for reporting the presence of myocardial bridging in a patient includes a data storage device storing instructions for reporting the presence of myocardial bridging in a patient; and a processor configured to execute the instructions to perform a method for reporting the presence of myocardial bridging, the method including: receiving patient-specific anatomical image data regarding a geometry of the patient's heart; creating a patient-specific model representing at least a portion of the patient's heart based on the patient-specific anatomical image data; detecting, within the patient-specific model, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

In accordance with another embodiment, a non-transitory computer readable medium for use on at least one computer system contains computer-executable programming instructions for performing a method for reporting the presence of myocardial bridging in a patient, the method comprising: receiving patient-specific anatomical image data regarding a geometry of the patient's heart; creating a patient-specific model representing at least a portion of the patient's heart based on the patient-specific anatomical image data; detecting, within the patient-specific model, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

In accordance with another embodiment, a computer-implemented method for assessing risk and hemodynamic significance of myocardial bridging in a patient includes obtaining a patient-specific model representing at least a portion of the patient's heart based on patient-specific anatomical image data regarding a geometry of the patient's heart; obtaining at least one estimate of at least one physiological and/or phenotypic parameter of the patient; defining at least one physiologic condition and/or at least one boundary condition of the patient in a physiologic stress state using the patient-specific model and the at least one estimate of at least one physiological and/or phenotypic parameter of the patient; evaluating a degree of myocardial bridging in the patient by identifying systolic compression of a coronary artery of the patient using the patient-specific model; performing computational fluid dynamics analysis on a myocardial bridging segment under simulated and/or dobutamine challenge conditions using the degree of myocardial bridging in the patient and the at least one physiologic condition and/or the at least one boundary condition of the patient; and computing at least one hemodynamic quantity of the myocardial bridging segment to evaluate risk based on the computational fluid dynamics and/or structural mechanics analysis.

In accordance with another embodiment, a system for assessing risk and hemodynamic significance of myocardial bridging in a patient includes a data storage device storing instructions for reporting the presence of myocardial bridging in a patient; and a processor configured to execute the instructions to perform a method including: obtaining a patient-specific model representing at least a portion of the patient's heart based on patient-specific anatomical image data regarding a geometry of the patient's heart; obtaining at least one estimate of at least one physiological and/or phenotypic parameter of the patient; defining at least one physiologic condition and/or at least one boundary condition of the patient in a physiologic stress state using the patient-specific model and the at least one estimate of at least one physiological and/or phenotypic parameter of the patient; evaluating a degree of myocardial bridging in the patient by identifying systolic compression of a coronary artery of the patient using the patient-specific model; performing computational fluid dynamics analysis on a myocardial bridging segment under simulated and/or dobutamine challenge conditions using the degree of myocardial bridging in the patient and the at least one physiologic condition and/or the at least one boundary condition of the patient; and computing at least one hemodynamic quantity of the myocardial bridging segment to evaluate risk based on the computational fluid dynamics analysis.

In accordance with another embodiment, a non-transitory computer readable medium for use on at least one computer system contains computer-executable programming instructions for performing a method for assessing risk and hemodynamic significance of myocardial bridging in a patient, the method including: obtaining a patient-specific model representing at least a portion of the patient's heart based on patient-specific anatomical image data regarding a geometry of the patient's heart; obtaining at least one estimate of at least one physiological and/or phenotypic parameter of the patient; defining at least one physiologic condition and/or at least one boundary condition of the patient in a physiologic stress state using the patient-specific model and the at least one estimate of at least one physiological and/or phenotypic parameter of the patient; evaluating a degree of myocardial bridging in the patient by identifying systolic compression of a coronary artery of the patient using the patient-specific model; performing computational fluid dynamics analysis on a myocardial bridging segment under simulated and/or dobutamine challenge conditions using the severity of myocardial bridging in the patient and the at least one physiologic condition and/or the at least one boundary condition of the patient; and computing at least one hemodynamic quantity of the myocardial bridging segment to evaluate risk based on the computational fluid dynamics analysis.

In accordance with another embodiment, a computer-implemented method for reporting the presence of myocardial bridging in a patient includes detecting, within a patient-specific model representing at least a portion of the patient's heart based on patient-specific anatomical image data regarding a geometry of the patient's heart, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

In accordance with another embodiment, a system for reporting the presence of myocardial bridging in a patient includes a data storage device storing instructions for reporting the presence of myocardial bridging in a patient; and a processor configured to execute the instructions to perform a method including: detecting, within a patient-specific model representing at least a portion of the patient's heart based on patient-specific anatomical image data regarding a geometry of the patient's heart, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

In accordance with another embodiment, a non-transitory computer readable medium for use on at least one computer system contains computer-executable programming instructions for performing a method for reporting the presence of myocardial bridging in a patient, the method includes: detecting, within a patient-specific model representing at least a portion of the patient's heart based on patient-specific anatomical image data regarding a geometry of the patient's heart, a segment of an epicardial coronary artery at least partially surrounded by the patient's myocardium to determine the presence of myocardial bridging; and computing, using at least one computer processor, at least one physical feature of the myocardial bridging to identify the severity of the myocardial bridging.

Additional embodiments and advantages will be set forth in part in the description which follows, and in part will be obvious from the description, or may be learned by practice of the disclosure. The embodiments and advantages will be realized and attained by means of the elements and combinations particularly pointed out below.

BRIEF DESCRIPTION OF THE DRAWINGS

The accompanying drawings, which are incorporated in and constitute a part of this specification, illustrate several embodiments and together with the description, serve to explain the principles of the disclosure.

DESCRIPTION OF THE EMBODIMENTS

Reference will now be made in detail to exemplary embodiments, examples of which are illustrated in the accompanying drawings. Wherever possible, the same reference numbers will be used throughout the drawings to refer to the same or like parts.

The present disclosure describes a non-invasive method to identify the presence of myocardial bridging in patients and assess the functional significance of myocardial bridging using a blood flow simulation under a simulated inotropic state of the myocardium. In doing so, the present disclosure provides a method to prescribe specific boundary conditions by modeling the systolic compression of a coronary artery observed in the tunneled segment. The methods described herein thus involve improvements in the diagnosis of the physiologic consequences of myocardial bridging and the prediction of the potential benefits or risks associated with alternate treatment strategies to correct the bridge or relieve ischemia.

The methods and systems disclosed herein use patient imaging to derive a patient-specific geometry of the blood vessels and myocardium, and combine this geometry with the patient-specific physiological information and boundary conditions to perform blood flow simulation for patients with myocardial bridging. For instance, the present disclosure provides systems and methods for: (i) reporting the presence of myocardial bridging; (ii) assessing the risk and hemodynamic significance of myocardial bridging under different physiologic states; and (iii) evaluating therapeutic options for treating myocardial bridging. Non-limiting, exemplary methods and systems for each category are described herein. Moreover, the systems and methods disclosed herein may optionally comprise determining at least one blood flow characteristic, such as FFR, of the myocardial bridging segment during systole and/or diastole using patient-specific model representing at least a portion of the patient's heart.

I. Report of Myocardial Bridging

Figure 1A:
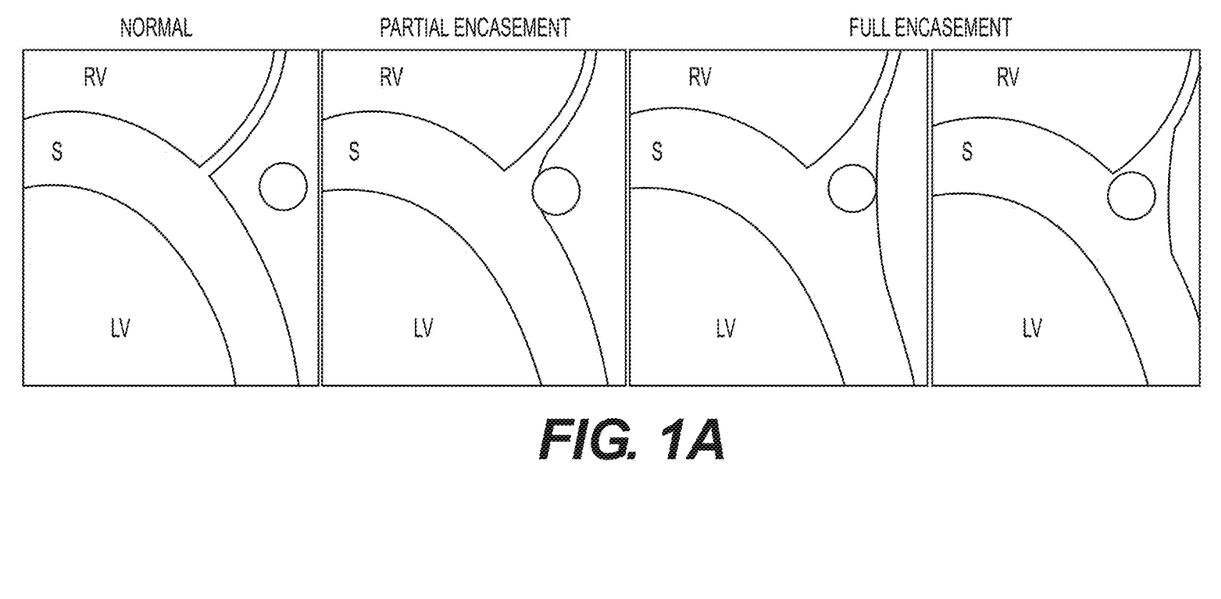
FIG. 1A is an exemplary diagram depicting a normal coronary artery, partial myocardial bridging, and full myocardial bridging.
Figure 1B:
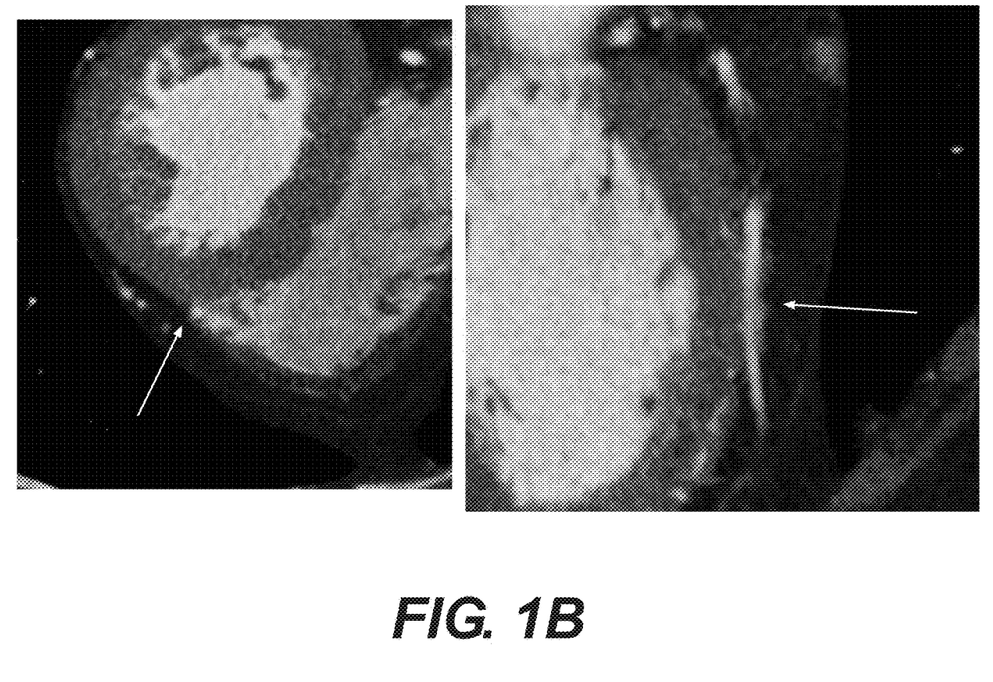
FIG. 1B shows an exemplary patient's cCTA images showing myocardial bridging, with the arrows indicating a segment of a coronary artery tunneling into a patient's myocardium.

FIG. 1A shows a normal coronary artery with no bridging, partial myocardial bridging of a coronary artery, and full myocardial bridging of a coronary artery. In FIG. 1A, "RV" indicates the right ventricle, "LV" indicates the left ventricle, and "S" indicates the septum. FIG. 1B depicts an exemplary patient's cCTA images showing myocardial bridging. The arrows point to a segment of a coronary artery encased in the patient's myocardium. The left image is a cross-sectional view of the area shown in the right image.

Figure 3:
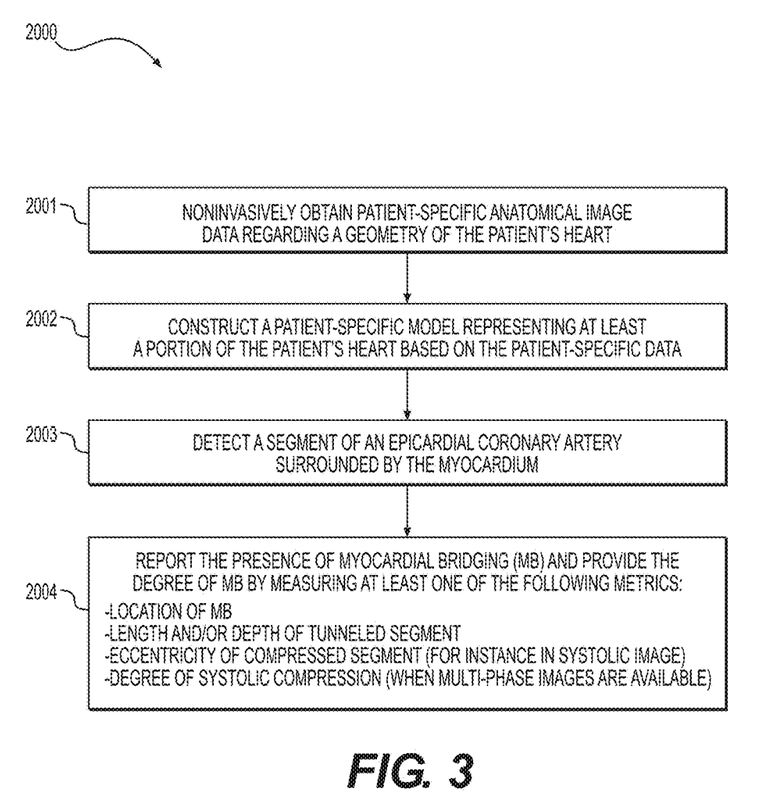
FIG. 3 is a flow chart of a method for reporting the presence of myocardial bridging, according to an exemplary embodiment.

FIG. 3 shows aspects of a method 2000 for reporting the presence of myocardial bridging, according to an exemplary embodiment. Systems and methods for reporting the presence of myocardial bridging may include, for example, obtaining patient-specific anatomical data, such as cardiac images of the patient (step 2001). Patient-specific anatomical data may be obtained non-invasively—e.g., via coronary computed tomographic angiography (cCTA) and/or magnetic resonance imaging (MRI). Moreover, patient-specific anatomical data may include data regarding the geometry of at least a portion of the patient's heart, e.g., at least a portion of the patient's aorta, a proximal portion of the main coronary arteries (and the branches extending therefrom) connected to the aorta, and the myocardium. Patients-specific anatomical data may be obtained via any of the methods described in U.S. Pat. No. 8,315,812, filed Jan. 25, 2011, and issued Nov. 20, 2012 ("the '812 patent"), the entire contents of which are incorporated herein by reference.

Figure 2:
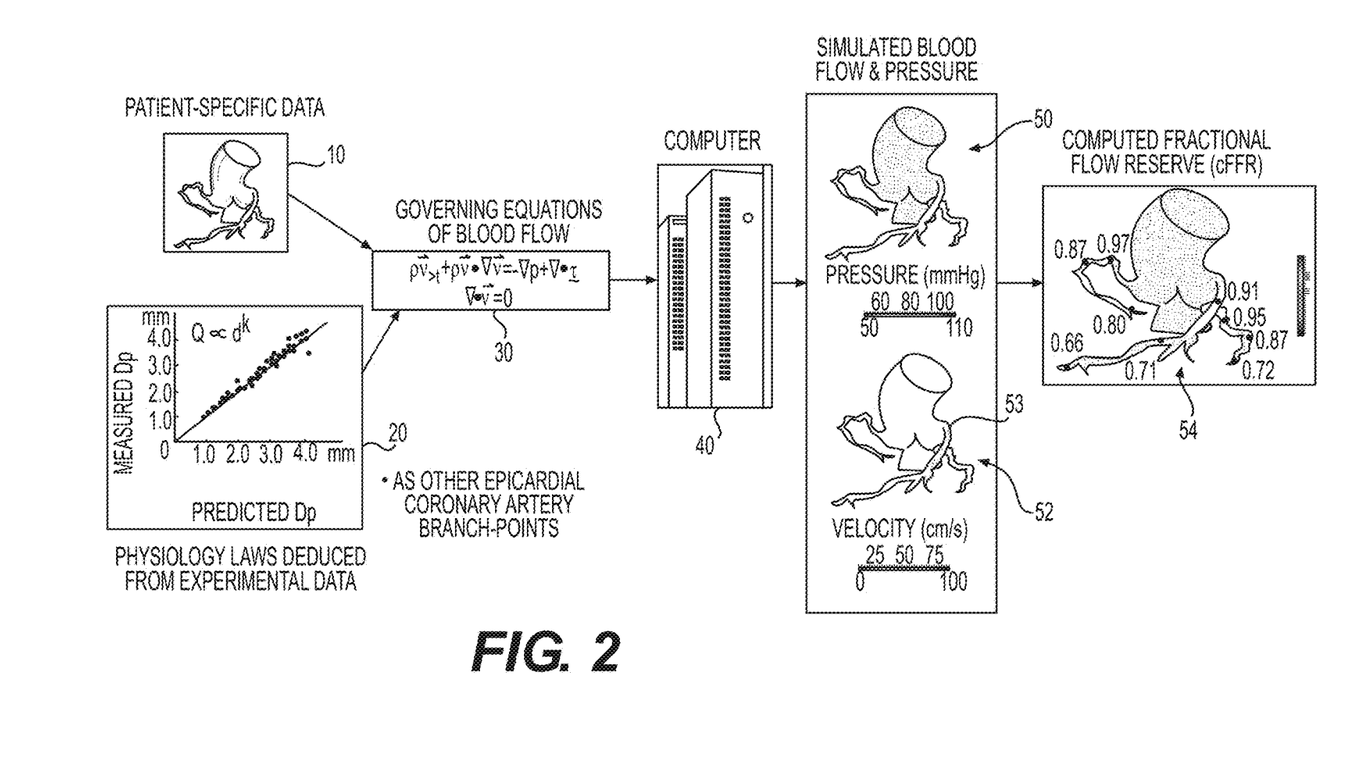
FIG. 2 is a schematic diagram of a system for providing various information relating to coronary blood flow in a specific patient, according to an exemplary embodiment.

Using the patient-specific anatomical data, method 2000 may comprise constructing a patient-specific model of at least a portion of the patient's heart, such as geometry of the patient's coronary arteries and the patient's myocardium (step 2002). In at least one embodiment, the patient-specific model may be chosen from a lumped-parameter model, a one-dimensional model, and a three-dimensional model. Patient-specific modeling may be performed, for example, using any of the methods described in the '812 patent. FIG. 2 shows aspects of a system for providing various information relating to coronary blood flow in a specific patient, according to an exemplary embodiment. A three-dimensional model 10 of the patient's anatomy may be created using data obtained noninvasively from the patient as will be described below in more detail. Other patient-specific information may also be obtained noninvasively. In an exemplary embodiment, the portion of the patient's anatomy that is represented by the three-dimensional model 10 may include at least a portion of the aorta and a proximal portion of the main coronary arteries (and the branches extending or emanating therefrom) connected to the aorta.

Various physiological laws or relationships 20 relating to coronary blood flow may be deduced, e.g., from experimental data as will be described below in more detail. Using the three-dimensional anatomical model 10 and the deduced physiological laws 20, a plurality of equations 30 relating to coronary blood flow may be determined as will be described below in more detail. For example, the equations 30 may be determined and solved using any numerical method, e.g., finite difference, finite volume, spectral, lattice Boltzmann, particle-based, level set, finite element methods, etc. The equations 30 may be solvable to determine information (e.g., pressure, velocity, FFR, etc.) about the coronary blood flow in the patient's anatomy at various points in the anatomy represented by the model 10.

The equations 30 may be solved using a computer 40. Based on the solved equations, the computer 40 may output one or more images or simulations indicating information relating to the blood flow in the patient's anatomy represented by the model 10. For example, the image(s) may include a simulated blood pressure model 50, a simulated blood flow or velocity model 52, a computed FFR (cFFR) model 54, etc., as will be described in further detail below. The simulated blood pressure model 50, the simulated blood flow model 52, and the cFFR model 54 provide information regarding the respective pressure, velocity, and cFFR at various locations along three dimensions in the patient's anatomy represented by the model 10. cFFR may be calculated as the ratio of the blood pressure at a particular location in the model 10 divided by the blood pressure in the aorta, e.g., at the inflow boundary of the model 10, under conditions of increased coronary blood flow, e.g., conventionally induced by intravenous administration of adenosine.

In an exemplary embodiment, the computer 40 may include one or more non-transitory computer-readable storage devices that store instructions that, when executed by a processor, computer system, etc., may perform any of the actions described herein for providing various information relating to blood flow in the patient. The computer 40 may include a desktop or portable computer, a workstation, a server, a personal digital assistant, or any other computer system. The computer 40 may include a processor, a read-only memory (ROM), a random access memory (RAM), an input/output (I/O) adapter for connecting peripheral devices (e.g., an input device, output device, storage device, etc.), a user interface adapter for connecting input devices such as a keyboard, a mouse, a touch screen, a voice input, and/or other devices, a communications adapter for connecting the computer 40 to a network, a display adapter for connecting the computer 40 to a display, etc. For example, the display may be used to display the three-dimensional model 10 and/or any images generated by solving the equations 30, such as the simulated blood pressure model 50, the simulated blood flow model 52, and/or the cFFR model 54.

Method 2000 may also comprise detecting a segment of an epicardial coronary artery at least partially surrounded by the patient's myocardium, to determine the presence of myocardial bridging (step 2003). In at least one embodiment, the epicardial coronary artery may be a major epicardial coronary artery. Step 2003 may include, for example, computing a signed distance map of the myocardial surface (inside: negative; outside: positive) and a signed distance map of the major epicardial coronary arteries, using the coronary and myocardium model from step 2002. Step 2003 may also include determining whether segments of epicardial coronary arteries belong to the negative distance map of the myocardial surface (i.e., inside the myocardium). If so, each such segment may be labeled as a myocardial bridging segment. Partial myocardial bridging may be measured by the following metrics: proportion of the surface area of the coronary artery that is inside the myocardium over the surface area of the total myocardial bridging segment; and/or proportion of the volume of the coronary artery that is inside the myocardium over the volume of the total myocardial bridging segment.

Method 2000 further may comprise reporting the presence of myocardial bridging and providing its severity by measuring one or more of the following severity metrics: location of myocardial bridging (e.g., start and end distance to the ostium); length and/or depth of the tunneled segment(s); eccentricity of the compressed segment(s) (such as in systolic image); and degree of systolic compression (when multiphase images are available) (step 2004). The severity of the myocardial bridging may be "scored" based on one or more of these severity metrics. For example, a higher myocardial bridging score may result from any of the following: more proximal myocardial bridging, deeper myocardial bridging, more eccentric myocardial bridging, and/or more systolic compression. The proximity of the myocardial bridging may be measured using the length and/or depth of the myocardial bridging segment. The depth of the myocardial bridging may be measured based on the eccentricity of the myocardial bridging segment cross-section measured by short axis length over long axis length. The eccentricity of the myocardial bridging, in turn, may be measured based on the degree of systolic compression (when multiphase images are available).

II. Assessment of Risk and Hemodynamic Significance of Myocardial Bridging

Figure 4:
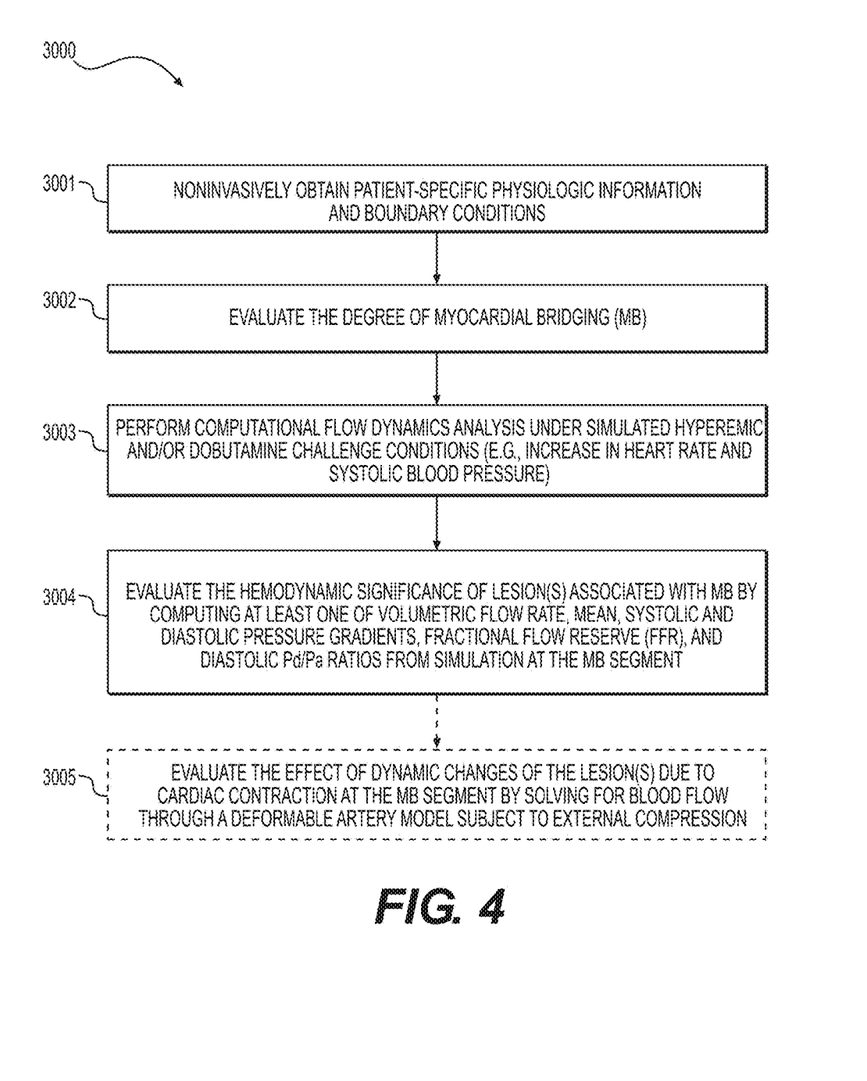
FIG. 4 is a flow chart of a method for assessing the risk and hemodynamic significance of myocardial bridging, according to an exemplary embodiment.

FIG. 4 shows aspects of a method 3000 for assessing risk and the hemodynamic significance of myocardial bridging, according to an exemplary embodiment. Method 3000 may comprise obtaining patient-specific physiologic information and boundary conditions (step 3001). Patient-specific physiologic information and boundary conditions may be obtained, for example, using any of the methods described in the '812 patent.

The severity of myocardial bridging may be evaluated (step 3002), using, for example, one or more of the metrics described above with respect to step 2004 of method 2000. Method 3000 may further comprise performing computational flow dynamics analysis under simulated hyperemic and/or dobutamine challenge conditions (e.g., increase in heart rate and/or systolic BP) (step 3003).

Method 3000 also may comprise evaluating the hemodynamic significance of one or more lesions associated with myocardial bridging by computing one or more of volumetric flow rate, averaged pressure gradient over cardiac cycles, systolic and diastolic pressure gradients, fractional flow reserve (FFR), and diastolic Pd/Pa ratios ("Pd" is coronary pressure distal to a myocardial bridging segment; "Pa" is coronary pressure proximal to a myocardial bridging segment) from simulation at the myocardial bridging segment (step 3004).

Optionally, method 3000 may further comprise evaluating the effect of dynamic changes of one or more lesions due to cardiac contraction at the myocardial bridging segment by solving, for example, for blood flow through a deformable artery model subject to external compression (optional step 3005). For example, optional step 3005 may include solving stress-equilibrium equations for a computational model of the coronary artery and external myocardium structures using fluid-structure interaction modeling techniques. The solution of structural mechanics of the coronary geometry in response to myocardial contraction may be solved iteratively along with the computational fluid dynamics (CFD). Alternatively, the fluid-structure interaction equations may be solved in a coupled manner using an arbitrary Lagrangian-Eulerian framework.

III. Evaluation of Therapeutic Options for Myocardial Bridging

Figure 5:
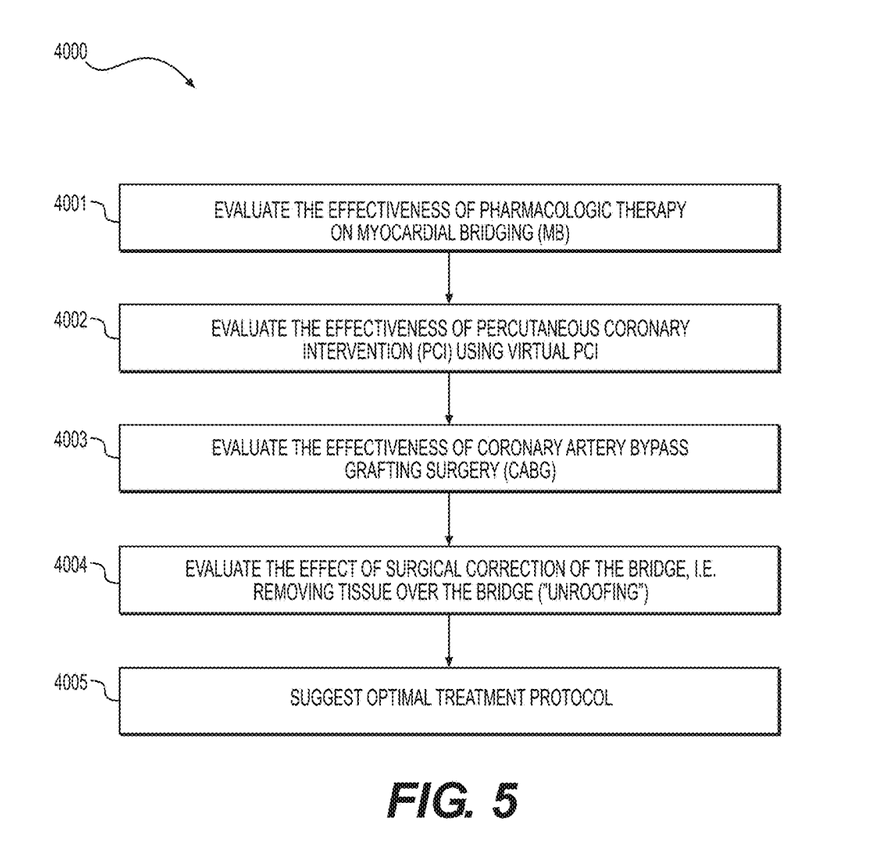
FIG. 5 is a flow chart of a method for evaluating therapeutic options for treating myocardial bridging, according to an exemplary embodiment.

FIG. 5 shows aspects of a method 4000 for evaluating therapeutic options for treating myocardial bridging, according to an exemplary embodiment. Method 4000 may comprise evaluating the effectiveness of pharmacologic therapy on myocardial bridging (step 4001). Method 4000 may also or alternatively comprise evaluating the effectiveness of percutaneous coronary intervention (PCI) using virtual PCI (step 4002). Method 4000 may further or alternatively comprise evaluating the effectiveness of coronary artery bypass grafting surgery (CABG) (step 4003). Method 4000 additionally or alternatively may comprise evaluating the effect of surgical correction of the bridge, i.e., removing tissue over the bridge, which may be termed "unroofing" (step 4004). Method 4000 also or alternatively may comprise suggesting an optimal treatment protocol (step 4005).

IV. Exemplary Embodiment

A non-limiting exemplary embodiment of a method and system for reporting a myocardial bridge and patient impact is provided below.

Reporting the Presence of Myocardial Bridging

Figure 6:
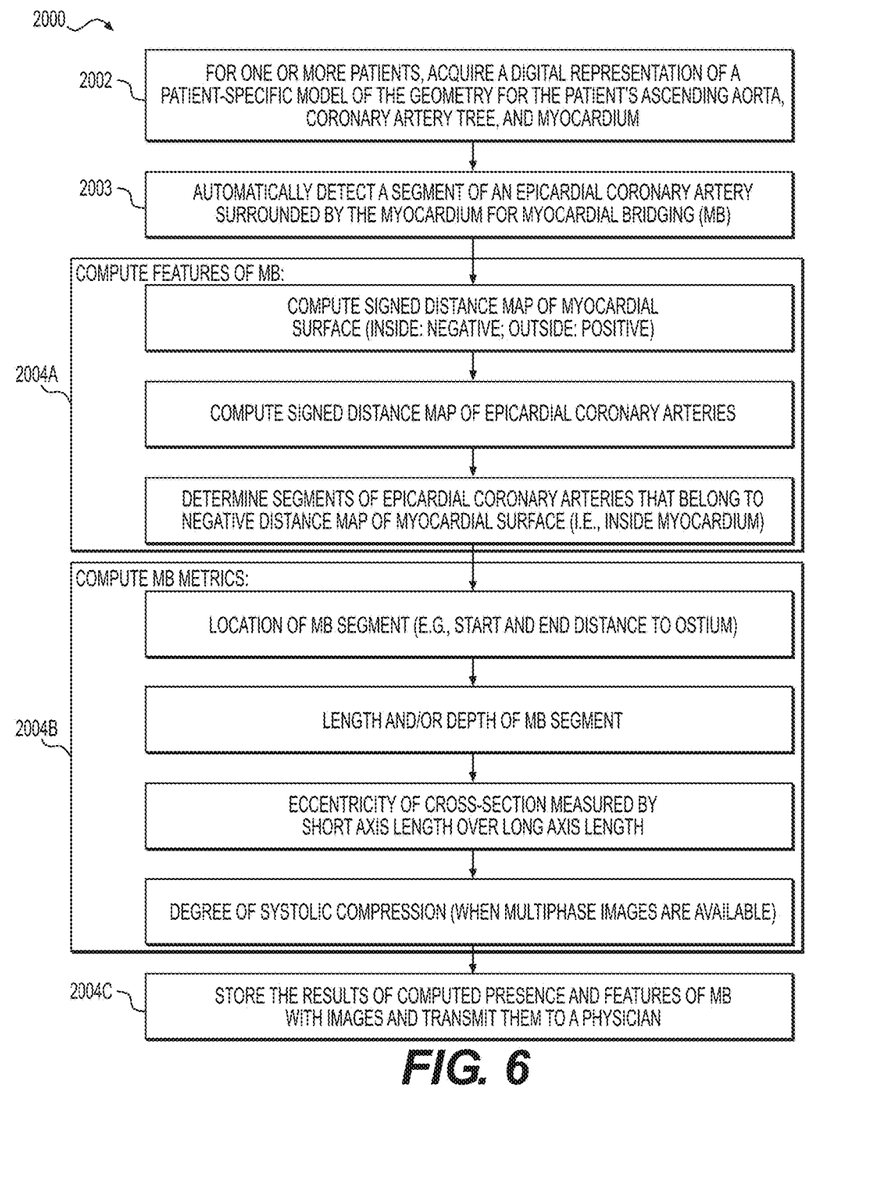
FIG. 6 is a flow chart of a method for reporting the presence of myocardial bridging, according to an exemplary embodiment.

FIG. 6 shows additional aspects of method 2000 for reporting the presence of myocardial bridging, according to an exemplary embodiment. Method 2000 may comprise, for example, acquiring, for one or more patients, a digital representation (e.g., the memory or digital storage [e.g., hard drive, network drive] of a computational device such as a computer, laptop, DSP, server, etc.) of a patient-specific model of the geometry for at least a portion of the patient's heart, such as the patient's ascending aorta, coronary artery tree, and myocardium (step 2002). This geometry may be represented as a list of points in space (possibly with a list of neighbors for each point) in which the space can be mapped to spatial units between points (e.g., millimeters), for example. This model may be derived, for example, by performing a cardiac computerized tomography (CT) scan in the end diastole phase of the cardiac cycle or using Magnetic Resonance Imaging (MRI). The image(s) may be segmented manually or automatically to identify voxels belonging to the lumen of the coronary arteries and myocardium. Inaccuracies in the geometry extracted automatically may be corrected by a human observer who compares the extracted geometry with the images and makes corrections as needed. Once the voxels are identified, the geometric model can be extracted (e.g., using marching cubes techniques). In at least one embodiment, the patient-specific model may be chosen from a lumped-parameter model, a one-dimensional model, and a three-dimensional model.

Using the constructed coronary and myocardium patient-specific model, method 2000 may comprise automatically detecting a segment of a epicardial coronary artery surrounded by the myocardium as exhibiting myocardial bridging (step 2003) and computing one or more features of myocardial bridging (step 2004). In at least one exemplary embodiment, the epicardial coronary artery may be a major epicardial coronary artery.

In at least one exemplary embodiment, step 2004 comprises computing one or more features of the detected myocardial bridging (step 2004A) and further computing one or more myocardial bridging metrics (step 2004B). Step 2004A, for example, may comprise computing a signed distance map of a myocardial surface, wherein the inside is negative and the outside is positive. Step 2004A may also comprise computing a signed distance map of one or more epicardial coronary arteries. In at least one embodiment, the one or more epicardial coronary arteries may be one or more major epicardial coronary arteries. Step 2004A may further comprise determining one or more segments of epicardial coronary arteries that belong to the negative distance map of the myocardial surface (i.e., inside the myocardium).

Step 2004B may comprise computing one or more of the following myocardial bridging metrics: the location of the myocardial bridging segment (e.g., start and end distance to the ostium); the length of the myocardial bridging segment; the depth of the myocardial bridging segment; the eccentricity of a cross-section of the myocardial bridging segment, which may be measured, for example, by short axis length over long axis length; and the degree of systolic compression (when multiphase images are available).

Method 2000 may further comprise storing the results of the computed presence and features of myocardial bridging with images (step 2004C). For example, the results may be saved as a digital representation (e.g., the memory or digital storage [e.g., hard drive, network drive] of a computational device such as a computer, laptop, DSP, server, etc.). Step 2004C may also comprise transmitting or making the results available to a health care provider, such as a physician.

Assessment of Risk and Hemodynamic Significance of Myocardial Bridging

Figure 7:
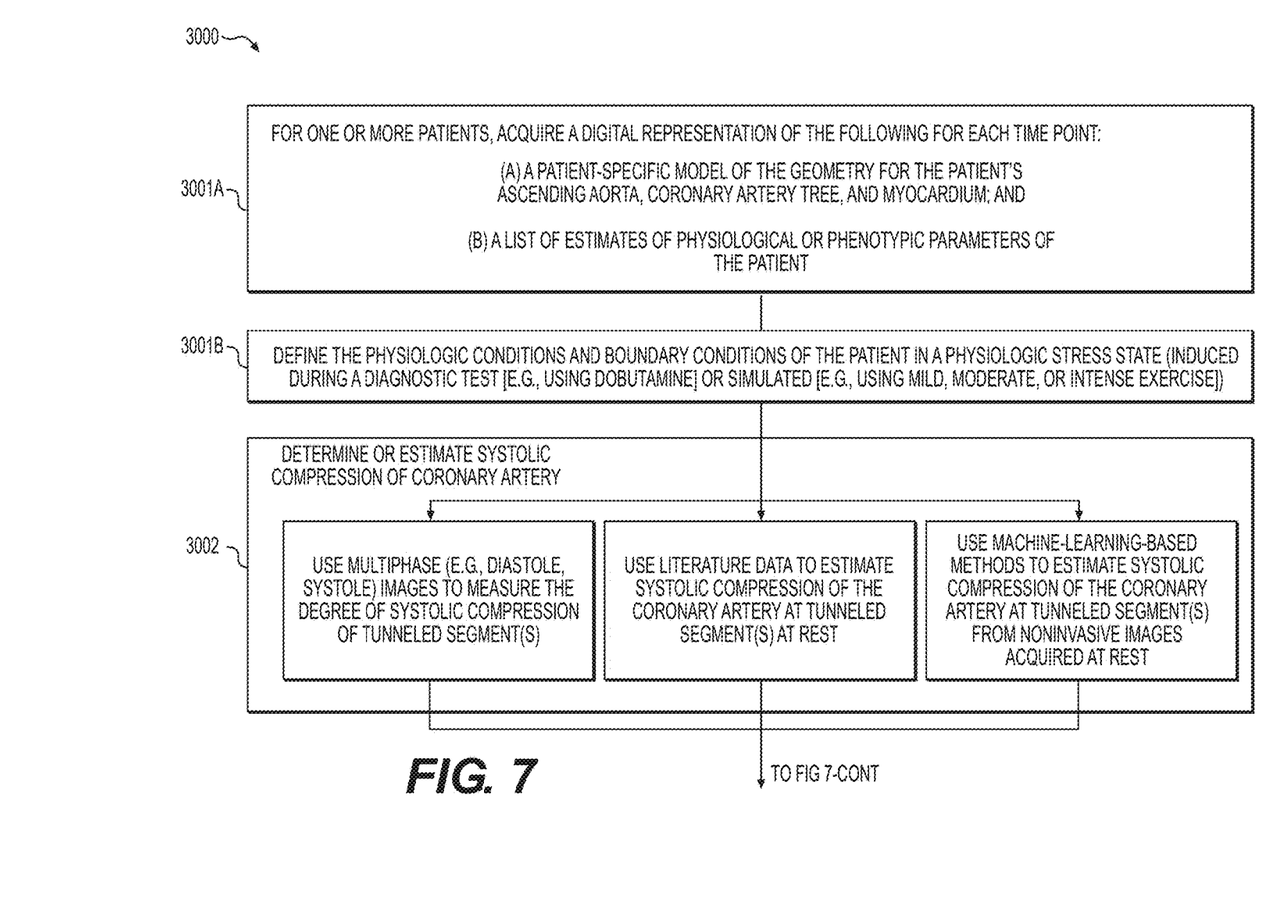
FIG. 7 is a flow chart of a method for assessing the risk and hemodynamic significance of myocardial bridging, according to an exemplary embodiment.

FIG. 7 shows additional aspects of method 3000 for assessing the risk and hemodynamic significance of myocardial bridging, according to an exemplary embodiment. The methods and systems described herein may employ, for example, computational fluid dynamics, fluid-structure interaction analysis, and/or machine-learning based estimations of systolic compression of coronary and physiologic boundary conditions to simulate hyperemic coronary flow and the inotropic state of the myocardium.

Method 3000 may comprise, for example, acquiring, for one or more patients, a digital representation (e.g., the memory or digital storage [e.g., hard drive, network drive] of a computational device such as a computer, laptop, DSP, server, etc.) of: (a) a patient-specific model of the geometry of at least a portion of the patient's heart, such as the patient's ascending aorta, coronary artery tree, and myocardium, for each time point and (b) a list of estimates of physiological or phenotypic parameters of the patient for each time point (step 3001A).

The geometry of at least a portion of the patient's heart, such as the patient's ascending aorta, coronary artery tree, and myocardium, may be represented as a list of points in space (possibly with a list of neighbors for each point, for example) in which the space can be mapped to spatial units between points (e.g., millimeters). The patient-specific model may be derived by performing a cardiac CT imaging of the patient in the end diastole phase of the cardiac cycle. The image then may be segmented manually or automatically to identify voxels belonging to the aorta and the lumen of the coronary arteries. Given a 3-D image of coronary vasculature, any method for extracting a patient-specific model of cardiovascular geometry may be used, including, for example, any of the methods described in the '812 patent. Inaccuracies in the geometry extracted automatically may be corrected by a human observer who compares the extracted geometry with the images and makes corrections as needed. Once the voxels are identified, the geometric model can be derived (e.g., using marching cubes). In at least one embodiment, the patient-specific model may be chosen from a lumped-parameter model, a one-dimensional model, and a three-dimensional model.

As non-limiting, exemplary examples, the list of estimates of physiological or phenotypic parameters of the patient may include one or more of: blood pressure; resting heart rate; hematocrit level; patient age and/or gender; myocardial mass, e.g., as derived by segmenting the myocardium in the image, calculating the volume in the image, and using an estimated density of 1.05 g/mL to estimate the myocardial mass; and general risk factors of coronary artery disease (e.g., smoking, diabetes, family history, weight, etc.).

Method 3000 may also comprise defining at least one physiologic condition and/or at least one boundary condition of the patient in a physiologic stress state (step 3001B). This stress state may be, for example, either one induced during a diagnostic test, e.g. using dobutamine, or simulated, e.g., using mild, moderate, or intense exercise. The at least one physiologic condition and/or at least one boundary condition of the patient under hyperemic conditions may be defined using the methods described in the '812 patent. Alternatively, the at least one physiologic condition and/or at least one boundary condition of the patient after treatment may be defined using the methods described in U.S. Pat. No. 8,249,815, filed Nov. 7, 2011, issued Aug. 21, 2012, the contents of which are incorporated herein by reference. The at least one physiologic condition and/or at least one boundary condition of the patient under an inotropic condition of the myocardium may be defined using the effect of dobutamine on the patient's physiology, such as an increase in heart rate and/or an increase in systolic pressure.

Method 3000 may comprise determining or estimating systolic compression of a coronary artery (step 3002). Step 3002 may be accomplished, for example, using multiphase (e.g., diastole, systole) images to measure the degree of systolic compression of tunneled segments. For instance, the degree of systolic compression may be measured by computing cross-sectional areas of myocardial bridging segments of the coronary surface meshes derived from the multiphase images. As another non-limiting example, step 3002 may be accomplished using literature data to estimate the systolic compression of a coronary artery at the tunneled segments at rest. For instance, literature data may teach a 71%+/−16% reduction of diameter within myocardial bridging as compared to a proximal/distal segment in systole, and a 35%+/−13% reduction of diameter in diastole. The patient geometry thus may be perturbed such that the myocardial bridging segments have a 71% reduction in diameter in systole and a 35% reduction in diastole. Specifically, the mesh coordinates of an identified myocardial bridging segment may be transformed in the perpendicular direction of the centerline with the proportions of 71%+/−16% and 35%+/−13% for systolic and diastolic phases, respectively.

Step 3002 may also be accomplished using machine-learning based methods to estimate the systolic compression of a coronary artery at tunneled segments from noninvasive images acquired at rest. Examples of machine learning methods are described, for example, in U.S. patent application Ser. No. 13/895,893, filed May 16, 2013, Ser. No. 13/895,871, filed May 16, 2013, and Ser. No. 14/011,151, filed Aug. 27, 2013, the contents of all of which are incorporated herein by reference.

An exemplary embodiment of a machine learning method is disclosed herein. The machine learning method may comprise a training mode and a prediction mode. In a training mode, the machine learning method may comprise creating a feature vector of the bridged artery from cCTA data. An exemplary feature vector may contain, for example: age, sex, heart rate, systolic and diastolic pressure, and/or epicardial fat volume; myocardial mass, regional density of myocardium, ejection fraction, and/or myocardial contractility; depth of coronary in relation to epicardium surface; and/or the length of the bridged segment. The machine learning method also may comprise associating this feature vector with invasive measurements of the bridged segment from imaging methods, such as angiography, intravascular ultrasound (IVUS), and optical coherence tomography (OCT). Non-limiting examples of invasive measurements include the depth and length of the bridged artery and the degree of systolic compression measured by change in diameter, area, and eccentricity of cross-sectional lumen. The machine learning method also may comprise training a machine learning algorithm (e.g., a linear Support Vector Machine) to the degree of systolic compression from the feature vectors obtained. The machine learning method further may comprise saving the results of the machine learning algorithm as a digital representation (e.g., memory or digital storage [e.g., hard drive, network drive] of a computational device such as a computer, laptop, DSP, server, etc.).

In the prediction mode, the machine learning method may comprise creating a feature vector of the bridged artery from cCTA data. The feature vector may be the same as the quantities used in the training mode. The machine learning method also may comprise using the saved results of the machine learning algorithm produced in the training mode (e.g., feature weights) to produce estimates of the degree of systolic compression. These estimates may be produced using the same machine learning technique used in the training mode. The machine learning method may comprise saving the estimated degree of systolic compression to a digital representation (e.g., memory or digital storage [e.g., hard drive, network drive] of a computational device such as a compute, laptop, DSP, server, etc.). The machine learning method further may comprise using the predicted degree of compression for a fluid-structure interaction simulation or reporting it to a health care provider, such as a physician.

Method 3000 may also comprise performing computational fluid dynamics analysis and/or structural mechanics simulation. This analysis may be performed using, for example, a three-dimensional finite element, finite volume, lattice Boltzman, level set, particle based method to solve the full equations of blood flow and pressure, and/or a fluid-structure interaction method to solve for at least one of blood flow, pressure and vessel wall motion, and deformation of the bridged segment (step 3003).

Method 3000 further may comprise computing at least one hemodynamic quantity of the myocardial bridging segment. For example, method 300 may comprise computing at least one of blood flow rate, averaged pressure gradient over cardiac cycles, systolic and diastolic pressure gradients, FFR over an entire cardiac cycle, and Pd/Pa over diastolic phase (step 3004). Step 3004 may also comprise computing wall shear stress at the myocardial bridging segment and/or the pressure gradient at the myocardial bridging segment.

Method 3000 may also comprise storing the results of the computed at least one hemodynamic quantity representing the risk of myocardial bridging with images (step 3006). For example, the results may be saved as a digital representation (e.g., the memory or digital storage [e.g., hard drive, network drive] of a computational device such as a computer, laptop, DSP, server, etc.). Step 3006 may further comprise transmitting or making the results available to a health care provider, such as a physician.

Evaluation of Therapeutic Options for Myocardial Bridging

Figure 8:
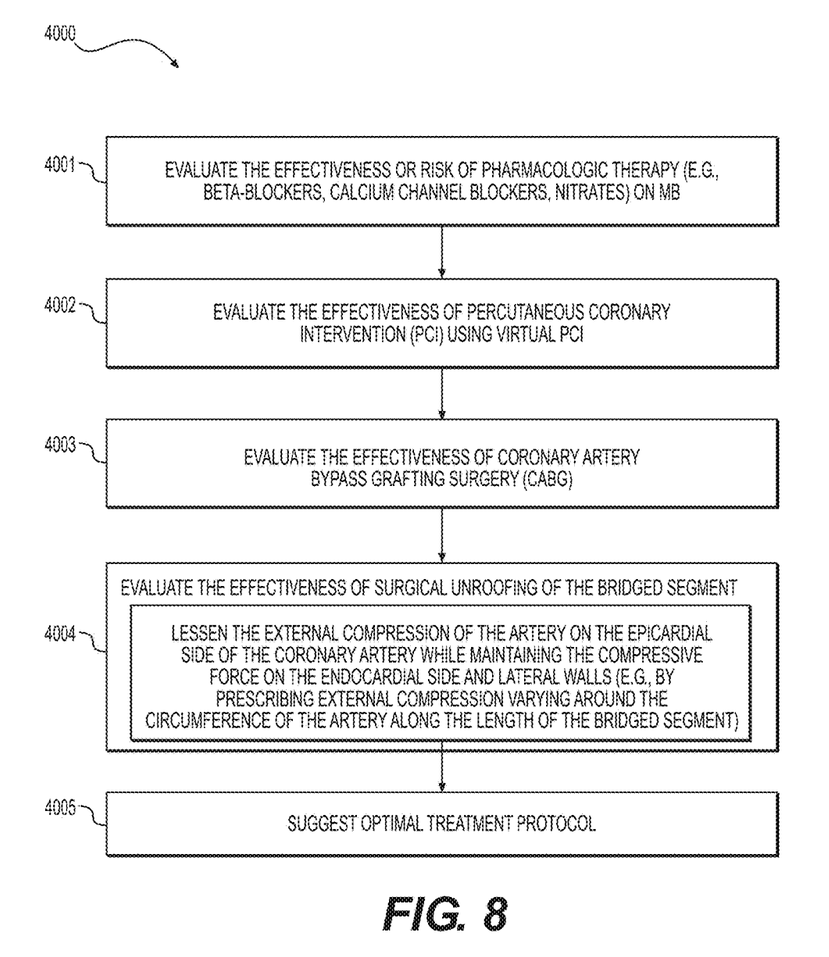
FIG. 8 is a flow chart of a method for evaluating therapeutic options for myocardial bridging, according to an exemplary embodiment.

FIG. 8 shows additional aspects of method 4000 for evaluating therapeutic options for myocardial bridging, according to an exemplary embodiment. The methods and systems for guiding treatment options disclosed herein may use a machine-learning based risk predictor established in previous steps by evaluating several therapeutic options for myocardial bridging.

In at least one embodiment, method 4000 may comprise evaluating the effectiveness or risk of pharmacologic therapy (e.g. beta-blockers, calcium channel blockers, and/or nitrates) on myocardial bridging (step 4001). For example, step 4001 may comprise iteratively updating the patient-specific model to simulate use of one or more pharmacologic therapies and evaluating the results. Modeling one or more pharmacologic therapies may be accomplished, for example, using any of the methods described in the '812 patent.

Method 4000 may also comprise evaluating the effectiveness of PCI using virtual PCI (step 4002). For example, step 4002 may comprise updating the patient-specific model to simulate insertion of one or more stents and evaluating the results. Modeling insertion of one or more stents may be accomplished, for example, using any of the methods described in the '812 patent.

In addition, method 4000 may comprise evaluating the effectiveness of coronary artery bypass grafting surgery (CABG) (step 4003). For example, step 4003 may comprise updating the patient-specific model to simulate surgically inserting at least one bypass and evaluating the results. Modeling bypass grafting surgery may be accomplished, for example, using any of the methods described in the '812 patent.

Method 4000 may further comprise evaluating the effectiveness of surgical unroofing of the bridged segment (step 4004). The effect of surgical unroofing of the bridged segment can be realized by lessening the external compression of the artery on the epicardial side of the coronary artery while maintaining the compressive force on the endocardial side and lateral walls. For example, this effect can be modeled by prescribing external compression varying around the circumference of the artery along the length of the bridged segment. Method 4000 may also comprise suggesting an optimal treatment protocol (step 4005).

Figure 9:
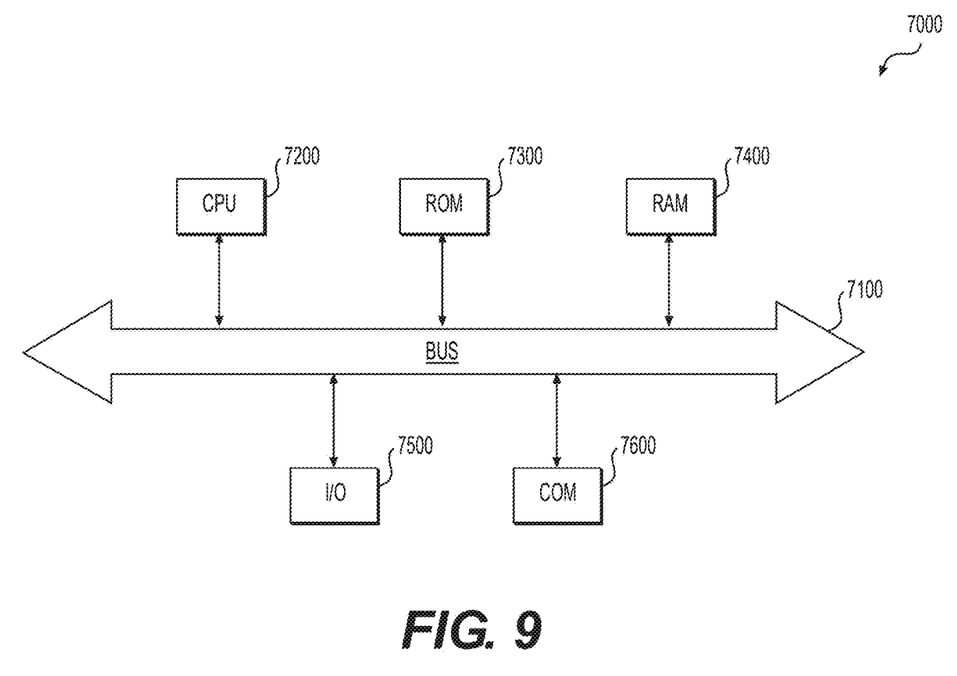
FIG. 9 is a block diagram of an exemplary computer system in which embodiments of the present disclosure may be implemented.

FIG. 9 provides a high-level functional block diagram illustrating an exemplary general-purpose computer 7000. Computer 7000 may be used to implement, for example, any of the methods described above. It is believed that those skilled in the art are familiar with the structure, programming, and general operation of such computer equipment and as a result, the drawings should be self-explanatory.

In an example, computer 7000 may represent a computer hardware platform for a server or the like. Accordingly, computer 7000 may include, for example, a data communication interface for packet data communication 7600. The platform may also include a central processing unit (CPU) 7200, in the form of one or more processors, for executing program instructions. The platform typically includes an internal communication bus 7100, program storage, and data storage for various data files to be processed and/or communicated by the platform such as ROM 7300 and RAM 7400, although the computer 7000 often receives programming and data via network communications 7700. The hardware elements, operating systems, and programming languages of such equipment are conventional in nature, and it is presumed that those skilled in the art are adequately familiar therewith. Computer 7000 also may include input and output ports 7500 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Any aspect set forth in any embodiment may be used with any other embodiment set forth herein. Every device and apparatus set forth herein may be used in any suitable medical procedure, may be advanced through any suitable body lumen and body cavity, and may be used for imaging any suitable body portion.

It will be apparent to those skilled in the art that various modifications and variations can be made in the disclosed systems and processes without departing from the scope of the disclosure. Other embodiments will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A computer-implemented method for determining risks of myocardial bridging in a patient, the method comprising:
receiving a plurality of patient-specific multiphase images;
generating, based on the plurality of multiphase images, a patient-specific mesh model of the patient's heart;
computing cross-sectional areas for one or more segments of the patient-specific mesh model;
computing, from the computed cross-sectional areas of the patient-specific mesh model, systolic compression of at least one selected segment of the segments of the patient-specific mesh model;
computing, at the at least one selected segment, a value of a hemodynamic characteristic using a computational fluid dynamics or structural mechanics analysis; and
outputting a coronary risk assessment for the patient or outputting a hemodynamic significance of the systolic compression in the patient-specific mesh model, based on the computed value of the hemodynamic characteristic.

2. The method of claim 1, wherein the hemodynamic characteristic includes blood flow rate, pressure gradient over cardiac cycles, systolic and diastolic pressure gradients, fractional flow reserve, and/or Pd/Pa.

3. The method of claim 1, wherein the patient-specific mesh model includes a geometry of the patient's ascending aorta, coronary artery tree, and myocardium.

4. The method of claim 1, further comprising:
computing the systolic compression further based on stored systolic compression associated with one or more individuals other than the patient.

5. The method of claim 4, further comprising:
receiving, for each of the one or more individuals, one or more characteristics including age, sex, heart rate, systolic pressure, diastolic pressure, epicardial fat volume, myocardial mass, regional density of myocardium, ejection fraction, myocardial contractility, depth of coronary artery in relation to epicardium surface, and/or a length of a bridged segment; and
computing a systolic compression associated with each of the received one or more characteristics, wherein the stored systolic compression is based on the computed systolic compression.

6. The method of claim 1, further comprising:
computing systolic compression associated with an individual other than the patient, based on the computed systolic compression at the at least one selected segment.

7. The method of claim 1, further comprising:
determining a physiologic condition associated with the patient; and
computing, at the at least one selected segment, the value of the hemodynamic characteristic using a computational fluid dynamics or structural mechanics analysis conducted at the determined physiologic condition.

8. The method of claim 1, further comprising:
determining a change in vessel diameter based on the computed cross-sectional area of the at least one selected segment;
computing the systolic compression at the at least one selected segment based on literature data associated with the determined change in vessel diameter.

9. The method of claim 1, further comprising:
outputting a treatment option for treating the at least one selected segment.

10. A system for reporting the presence of myocardial bridging in a patient, the system comprising:
a data storage device storing instructions for reporting the presence of myocardial bridging in a patient; and
a processor configured to execute the instructions to perform a method including:
receiving a plurality of patient-specific multiphase images;
generating, based on the plurality of multiphase images, a patient-specific mesh model of the patient's heart;
computing cross-sectional areas for one or more segments of the patient-specific mesh model;
computing, from the computed cross-sectional areas of the patient-specific mesh model, systolic compression of at least one selected segment of the segments of the patient-specific mesh model;
computing, at the at least one selected segment, a value of a hemodynamic characteristic using a computational fluid dynamics or structural mechanics analysis; and
outputting a coronary risk assessment for the patient or outputting a hemodynamic significance of the systolic compression in the patient-specific mesh model, based on the computed value of the hemodynamic characteristic.

11. The system of claim 10, wherein the hemodynamic characteristic includes blood flow rate, pressure gradient over cardiac cycles, systolic and diastolic pressure gradients, fractional flow reserve, and/or Pd/Pa.

12. The system of claim 10, wherein the patient-specific mesh model includes a geometry of the patient's ascending aorta, coronary artery tree, and myocardium.

13. The system of claim 12, wherein the system is further configured for:
computing the systolic compression further based on stored systolic compression associated with one or more individuals other than the patient.

14. The system of claim 13, wherein the system is further configured for:
receiving, for each of the one or more individuals, one or more characteristics including age, sex, heart rate, systolic pressure, diastolic pressure, epicardial fat volume, myocardial mass, regional density of myocardium, ejection fraction, myocardial contractility, depth of coronary artery in relation to epicardium surface, and/or a length of a bridged segment; and
computing a systolic compression associated with each of the received one or more characteristics, wherein the stored systolic compression is based on the computed systolic compression.

15. The system of claim 10, wherein the system is further configured for:
computing systolic compression associated with an individual other than the patient, based on the computed systolic compression at the at least one selected segment.

16. The system of claim 10, wherein the system is further configured for:
determining a physiologic condition associated with the patient; and
computing, at the at least one selected segment, the value of the hemodynamic characteristic using a computational fluid dynamics or structural mechanics analysis conducted at the determined physiologic condition.

17. The system of claim 10, wherein the system is further configured for:
determining a change in vessel diameter based on the computed cross-sectional area of the at least one selected segment;
computing the systolic compression at the at least one selected segment based on literature data associated with the determined change in vessel diameter.

18. A non-transitory computer readable medium for use on at least one computer system containing computer-executable programming instructions for performing a method for reporting the presence of myocardial bridging in a patient, the method comprising:
receiving a plurality of patient-specific multiphase images;
generating, based on the plurality of multiphase images, a patient-specific mesh model of the patient's heart;
computing cross-sectional areas for one or more segments of the patient-specific mesh model;
computing, from the computed cross-sectional areas of the patient-specific mesh model, systolic compression of at least one selected segment of the segments of the patient-specific mesh model;
computing, at the at least one selected segment, a value of a hemodynamic characteristic using a computational fluid dynamics or structural mechanics analysis; and
outputting a coronary risk assessment for the patient or outputting a hemodynamic significance of the systolic compression in the patient-specific mesh model, based on the computed value of the hemodynamic characteristic.

19. The non-transitory computer readable medium of claim 18, wherein the hemodynamic characteristic includes blood flow rate, pressure gradient over cardiac cycles, systolic and diastolic pressure gradients, fractional flow reserve, and/or Pd/Pa.

20. The non-transitory computer readable medium of claim 18, wherein the patient-specific mesh model includes a geometry of the patient's ascending aorta, coronary artery tree, and myocardium.

* * * * *